(12) United States Patent
Shen et al.

(10) Patent No.: US 10,161,869 B2
(45) Date of Patent: *Dec. 25, 2018

(54) EVALUATING SOLID PARTICLE SEPARATION IN WELLBORE FLUIDS

(71) Applicant: Halliburton Energy Services, Inc., Houston, TX (US)

(72) Inventors: Rui Shen, Humble, TX (US); Timothy N. Harvey, Humble, TX (US); Dale E. Jamison, Humble, TX (US); Cato Russell McDaniel, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/517,679

(22) PCT Filed: Nov. 25, 2014

(86) PCT No.: PCT/US2014/067355
§ 371 (c)(1),
(2) Date: Apr. 7, 2017

(87) PCT Pub. No.: WO2016/085469
PCT Pub. Date: Jun. 2, 2016

(65) Prior Publication Data
US 2017/0307526 A1 Oct. 26, 2017

(51) Int. Cl.
*G01N 21/51* (2006.01)
*E21B 49/08* (2006.01)
(Continued)

(52) U.S. Cl.
CPC ............ *G01N 21/51* (2013.01); *E21B 41/00* (2013.01); *E21B 49/08* (2013.01);
(Continued)

(58) Field of Classification Search
CPC .. G01N 15/0631; G01N 21/51; G01N 15/082; G01N 2021/4709; G01N 21/532;
(Continued)

(56) References Cited

U.S. PATENT DOCUMENTS

| 3,713,743 A | 1/1973 | Simms |
| 4,152,070 A | 5/1979 | Kushner et al. |

(Continued)

FOREIGN PATENT DOCUMENTS

| CA | 2806479 | 6/2010 |
| JP | 2006047166 | 2/2006 |
| WO | 2014062670 | 4/2014 |

OTHER PUBLICATIONS

International Search Report and Written Opinion for PCT/US2014/067355 dated Jul. 29, 2015.
Wikipedia definition of Turbidimetry dated Sep. 17, 2013.

*Primary Examiner* — Isiaka Akanbi
(74) *Attorney, Agent, or Firm* — Tenley Kreuger Tumey L.L.P.

(57) ABSTRACT

Turbidity measurement systems and methods of using the same are described. A turbidity measurement system comprise a vessel configured to hold a wellbore fluid, wherein a permeable obstruction to flow is positioned in the vessel; a light source positioned to direct light at the vessel; a light detector positioned to measure light intensity of light emitted by the light source and passing through the vessel; and a backscatter detector positioned to measure the light intensity of reflected light emitted from the light source.

17 Claims, 3 Drawing Sheets

(51) Int. Cl.
    *E21B 41/00*     (2006.01)
    *G01N 15/08*     (2006.01)
    *G01V 8/12*      (2006.01)
    *G01N 21/47*     (2006.01)

(52) U.S. Cl.
    CPC .......... *G01N 15/0806* (2013.01); *G01V 8/12*
         (2013.01); *E21B 2049/085* (2013.01); *G01N 2015/084* (2013.01); *G01N 2021/4709* (2013.01); *G01N 2021/513* (2013.01)

(58) Field of Classification Search
    CPC ...... G01N 21/253; G01N 21/85; G01B 11/06; E21B 47/102
    USPC .................. 356/342, 335–336, 445, 343
    See application file for complete search history.

(56) References Cited

U.S. PATENT DOCUMENTS

| | | | |
|---|---|---|---|
| 5,403,497 A | 4/1995 | Schultz | |
| 5,940,178 A | 8/1999 | Barber et al. | |
| 6,795,183 B2* | 9/2004 | O'Keeffe | G01N 15/0205 356/338 |
| 2009/0299651 A1 | 12/2009 | Sadar | |
| 2014/0038857 A1 | 2/2014 | Miller et al. | |
| 2014/0166361 A1* | 6/2014 | Jamison | E21B 21/065 175/24 |
| 2016/0370287 A1* | 12/2016 | Barnes | G01N 21/05 |

\* cited by examiner

EVALUATING SOLID PARTICLE SEPARATION IN WELLBORE FLUIDS

BACKGROUND

Embodiments are directed to methods and systems for evaluating the solid particle separation of wellbore fluids, and more particularly, embodiments disclose using turbidimetry to measure the separation of solids from wellbore fluids as the wellbore fluids flow across a permeable obstruction, such as porous media and fractured media.

Solid removal processes and solids control systems may be an important aspect of wellbore fluid treatment. For example, the removal of solids from drilling fluids may be important to maintain the integrity of the fluid. If solids are not sufficiently removed from the drilling fluid, the amount of drilling fluid that may be reused may be reduced, resulting in additional operations expenditures. Further, higher than normal concentrations of solids in wellbore fluids may require additional amounts of said wellbore fluids to dilute the solids so that they do not impact wellbore operations. The need for additional amounts of wellbore fluids may also result in additional operations expenditures. Additionally, wellbore fluids may be lost to lost circulation zones, also known as thief zones, in the subterranean formation. If a lost circulation zone is not successfully bridged, wellbore fluid may be lost, pressure may be lost, and the formation could potentially be damaged. Finally, in operations using hydraulic fracturing, the choice of proppant can impact the effectiveness of the fracturing operation. Choosing a proppant that is incapable of build-up within a fracture or is incapable of propping a fracture may result in the fracture closing, thereby causing a loss in the recovery of valuable hydrocarbons from the fracture.

Generally the removal of solids or the loss of fluid may be measured through the monitoring of the pressure-flow characteristics of the wellbore fluid. However, this evaluation requires input parameters by calibration and calculation and cannot be used to measure the dynamic separation process. In the case of testing the effectiveness of bridging lost circulation zones, American Petroleum Institute Recommended Practice 13B-1 Annex J and/or 13B-2 Annex L may be used. However, these practices may be limited in scope in that they do typically not allow for analysis of the dynamics of particle build-up within and above the lost circulation zone. Similarly to the measurement of the effectiveness of lost circulation materials, current applications for testing the effectiveness of proppant build-up in a fracture also may not allow for analysis of the dynamics of particle build-up within the fracture.

BRIEF DESCRIPTION OF THE DRAWINGS

These drawings illustrate certain aspects of some of the embodiments of the present invention, and should not be used to limit or define the invention.

DETAILED DESCRIPTION

Embodiments are directed to methods and systems for evaluating the solid particle separation of wellbore fluids, and more particularly, embodiments disclose using turbidimetry to measure the separation of solids from wellbore fluids as the wellbore fluids flow across a permeable obstruction, such as porous media and fractured media.

Generally, the methods and systems disclosed herein may comprise one or more turbidity measurement apparatuses. Turbidity measurement apparatuses, also commonly referred to as turbimeters or more generally as nephelometers, may be used to measure the turbidity of a liquid. These apparatuses may pass a known wavelength of light through a wellbore fluid and then may measure the intensity of the transmitted light as well as the light backscattered by the wellbore fluid. This process ultimately produces a measurement of the absorbed light that can be used to determine the turbidity level of the wellbore fluid. The turbidity of the wellbore fluid may be correlated with the amount of suspended solids in the wellbore fluid. As such, this analysis may allow for the study of the dynamics of the suspended solids in the wellbore fluid.

The turbidity measurement apparatus may generally comprise a light emitter and a light detector. Further, the methods and systems may additionally utlilize a wellbore fluid. The wellbore fluid may be a sample from any such wellbore fluid for use in a wellbore. The wellbore fluid may additionally comprise suspended solids. Generally, the suspended solids in the wellbore fluid may be measured by the turbidity measurement apparatus. The wellbore fluid may be placed into a vessel containing a permeable obstruction, such as a porous media or fractured media. Pressure may be applied to force the wellbore fluid through the permeable obstruction and/or into the permeable obstruction. Depending on the permeable obstruction, the wellbore fluid, and the test conditions, solids from the wellbore fluid may be filtered by the permeable obstruction, solids from the wellbore fluid may form a filter cake on the face of the permeable obstruction, and/or solids from the wellbore solids may pack one or more fractures in the permeable obstruction. The measurements of the suspended solids in the wellbore fluid, the filter cake, and/or pack formed by the solids and/or filter cake may be used to analyze the effectiveness of the porous media (e.g., filters) or suspended solids in the wellbore fluid, and additionally the measurements may be used to analyze the permeability or porosity of a formation or fracture in a formation.

Figure 1:
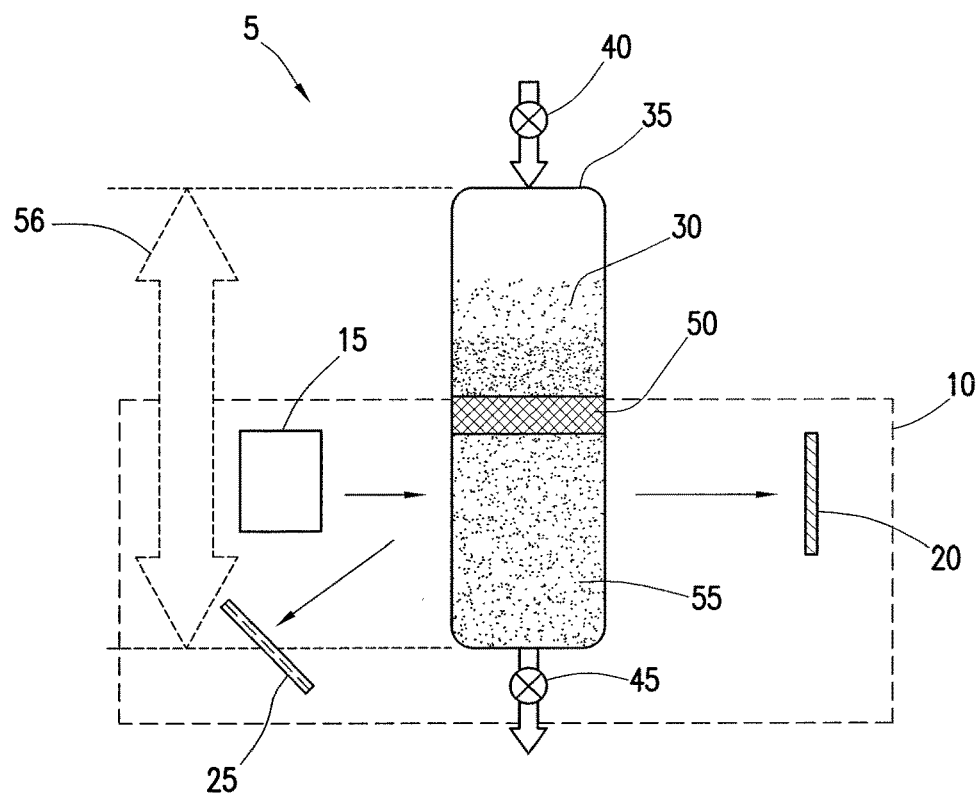
FIG. 1 is an illustration depicting an example turbidity measurement system used to measure the effectiveness of a filtration process.

FIG. 1 is an illustration depicting an example turbidity measurement system 5 used to measure the effectiveness of a filtration process. Turbidity measurement system 5 may comprise a turbidity measurement apparatus 10, which, for ease of illustration is generally illustrated as a collective of its component parts. Turbidity measurement apparatus 10 may generally comprise a light source 15 and a light detector 20. Optionally, turbidity measurement apparatus 10 may also comprise a backscatter detector 25. Turbidity measurement apparatus 10 may comprise a single unit wherein all of the component pieces or disposed within or about the single unit. Alternatively, turbidity measurement apparatus 10 may be formed from individual modules comprising one or more of the components of turbidity measurement apparatus 10 that are connected in a manner sufficient to form a functioning turbidity measurement apparatus 10.

Light source 15 may be any such light source sufficient for use with turbidity measurement apparatus 10. Light source 15 is not to be restricted to the emission of visible light, but may also emit any suitable wavelength of electromagnetic radiation including full spectrum light, infrared, ultraviolet light A, ultraviolet light B, ultraviolet light C, etc. For example, light source 15 may emit light of a wavelength in a range of 600 nm to 1000 nm. Light source 15 may comprise any source of light including, without limitation, filaments, bulbs, lasers, fiber optics, light emitting diodes, and the like. Light source 15 may optionally comprise a filter (not shown) to select for a specific wavelength of light. Turbidity measurement apparatus 10 may comprise more than one light source 15, and light source(s) 15 may be positioned at any desirable angle. With the benefit of this disclosure, one having ordinary skill in the art will be able to select a suitable light source for use with the methods and systems disclosed herein.

Light detector 20 and backscatter detector 25 may be any light detectors sufficient for use with turbidity measurement apparatus 10. As used herein, light detector 20 describes a light detector that measures the intensity of light transmitted from the light source 15 through a wellbore fluid to light detector 20. Whereas backscatter detector 25, as used herein, describes a light detector that measures the intensity of the light reflected from reflective particles in a wellbore fluid as light source 15 transmits light through the wellbore fluid. Thus, the difference between light detector 20 and backscatter detector 25 is a matter of the positioning of the detectors. Light detector 20 and backscatter detector 25 may comprise the same type of light detector or may comprise different types of light detectors. Without limitation, examples of light detectors may include radiometers, photometers, photodetectors, photonic detectors, photovoltaics, photoconductive detectors, phototransistors, photodiodes, and the like. Turbidity measurement apparatus 10 may comprise more than one light detector 20 and/or backscatter detector 25. Light detector 20 and backscatter detector 25 may be positioned at any desirable angle, with the caveat that the positioning of light detector 20 and backscatter detector 25 must be relative to light source 15 so that any light detector 20 and backscatter detector 25 may be able to adequately detect and measure the intensity of the light emitted by the light source 15. With the benefit of this disclosure, one having ordinary skill in the art will be able to select a suitable light detector and backscatter detector for use with the methods and systems disclosed herein.

With continued reference to FIG. 1, turbidity measurement system 5 additionally comprises a wellbore fluid 30. Wellbore fluid 30 may be any such wellbore fluid in which the dynamics of the flow and separation of solids is desirable. Without limitation, examples of wellbore fluid 30 include drilling fluids, fracturing fluids, lost circulation fluids, displacement fluids, drill-in fluids, and any type of treatment fluid. Wellbore fluid 30 may comprise solids. The solids may be any such solids found in a wellbore or introduced into a wellbore fluid. Without limitation, examples of solids include, pieces of the formation, drill cuttings, and additives introduced to a wellbore fluid, e.g., lost circulation materials, proppants, etc. The solids may comprise any such particle size and shape. Of particular relevance may be solids that are too small for gravitational or centrifugal separation methods. Some of the solids suspended in wellbore fluid 30 may reflect light emitted by light source 15. The reflected light may be detected and measured by one or more backscatter detectors 25. With the benefit of this disclosure, one having ordinary skill in the art will be able to recognize suitable wellbore fluids for use with the methods and systems disclosed herein.

FIG. 1 further depicts the injection of wellbore fluid 30 into a vessel 35. Vessel 35 may be any such vessel suitable for containing wellbore fluid 30 and for allowing light emitted from light source 15 to pass through. Because light detector 20 and backscatter detector 25 measure the intensity of light passing through or reflected by solids within wellbore fluid 30, it is important that vessel 35 containing wellbore fluid 30 not diminish or otherwise alter the intensity of the light to be measured. Thus, preferred embodiments of vessel 35 comprise materials that are transparent or nearly transparent and that have little to no reflective characteristics. Examples of materials may include, but should not be limited to, glass or transparent plastics, for example, acrylic. Vessel 35 may be any size and shape, for example vessel 35 may be a cylinder, cubic, etc. Vessel 35 may comprise an injection port 40 and a filtrate port 45. Injection port 40 may comprise any type of port sufficient for allowing wellbore fluid 30 to be introduced to the interior of vessel 35. Filtrate port 45 may comprise any type of port sufficient allowing the filtrate of wellbore fluid 30 to exit the interior of vessel 35. With the benefit of this disclosure, one having ordinary skill in the art will be able to select a suitable vessel for use with the methods and systems disclosed herein.

Within vessel 35, filter 50 may be disposed. Filter 50 may be any such filter used to remove solids from wellbore fluid 30. As discussed above, after wellbore fluid 30 is passed through filter 50, the filtrate 55 of wellbore fluid 30 may exit vessel 35 via filtrate port 45. The filtrate 55 of wellbore fluid 30 may comprise fewer solids than wellbore fluid 30. Filter 50 may be a filter used with a high-pressure, high-temperature filtration system. Filter 50 may have any desired porosity. Pressure may be applied to wellbore fluid 30 in order to force wellbore fluid 30 through filter 50. Alternatively, no pressure may be applied to wellbore fluid 30 and the gravitational pull on wellbore fluid 30 may be sole method of passing wellbore fluid 30 through filter 50. A commercial example of filter 50 is the Series 300 API Low Pressure Low Temperature (LPLT) Filter Press, available from Fann® Instrument Company, Houston, Tex. Working pressure of this system is 100 psig and the filtering area is 7.1-in$^2$, as specified in the American Petroleum Institute, API Recommended Practice 13B-1 and 13B-2. An example of the filter is the filter paper recommended by API 13B-2. With the benefit of this disclosure, one having ordinary skill in the art will be able to select a suitable filter for use with the methods and systems disclosed herein.

With continued reference to FIG. 1, turbidity measurement apparatus 10 may measure the filtration efficiency of filter 50 by measuring the intensity of the light passing through wellbore fluid 30 as well as the intensity of the light reflected by any solids within wellbore fluid 30. The data obtained from this measurement may show the amount that the light emitted by light source 15 is diminished by reflection due to the presence of solids suspended in wellbore fluid 30. Thus, the reduction in light intensity data may be used to determine the turbidity of the wellbore fluid 30. This turbidity measurement may be compared with a second turbidity measurement obtained by measuring intensity of the light passing through the filtrate 55 of wellbore fluid 30 as well as the intensity of the light reflected by any solids within the filtrate 55 of wellbore fluid 30. By comparison of the turbidity level of the wellbore fluid 30 prior to filtration by filter 50 with the turbidity level of the filtrate 55 of wellbore fluid 30, the effectiveness of filter 50 at reducing the turbidity level and thus the amount of solids suspended in wellbore fluid 30 may be deduced. The above description describes a simplified view of the overall process where only measurement on either side of the filer 50 is obtained. However, the turbidity measurement apparatus 10 may scan a portion of, or the entirety of the length and/or width of the vessel 35 as illustrated by arrow 56 and then use the measurements of the scan to capture the filtration efficiency of filter 50 in real time. This method may comprise taking multiple measurements of wellbore fluid 30 and filtrate 55. Further, the scan of the length and/or width of the vessel 35 may be continuous so that turbidity measurement apparatus 10 continuously scans the length and/or width of the vessel 35 providing real time updates of the efficiency of filter 50 over time. Lastly, the entire process may be a continuous flow process or may be a batch process. In a continuous flow process, wellbore fluid 30 may be continuously injected via injection port 40 into vessel 35 and may be continuously scanned by turbidity measurement apparatus 10 as it enters vessel 35, passes through filter 50, and exits vessel 35 via filtrate port 45. Thus, turbidity measurement apparatus 10 is able to obtain real time measurements of wellbore fluid 30 as it is continuously filtered by filter 50. Such measurements may be important for determining whether a wellbore fluid 30 may be reused or whether a wellbore fluid 30 needs to be diluted. A batch process does not use continuous flow injection of wellbore fluid 30, but may use continuous scanning by turbidity measurement apparatus 10. In a batch process example, a set amount of wellbore fluid 30 is injected into vessel 35 and measured by turbidity measurement apparatus 10. Measurements obtained from a batch process may be important for determining the experimental effectiveness of a filter prior to use in the field.

Figure 2:
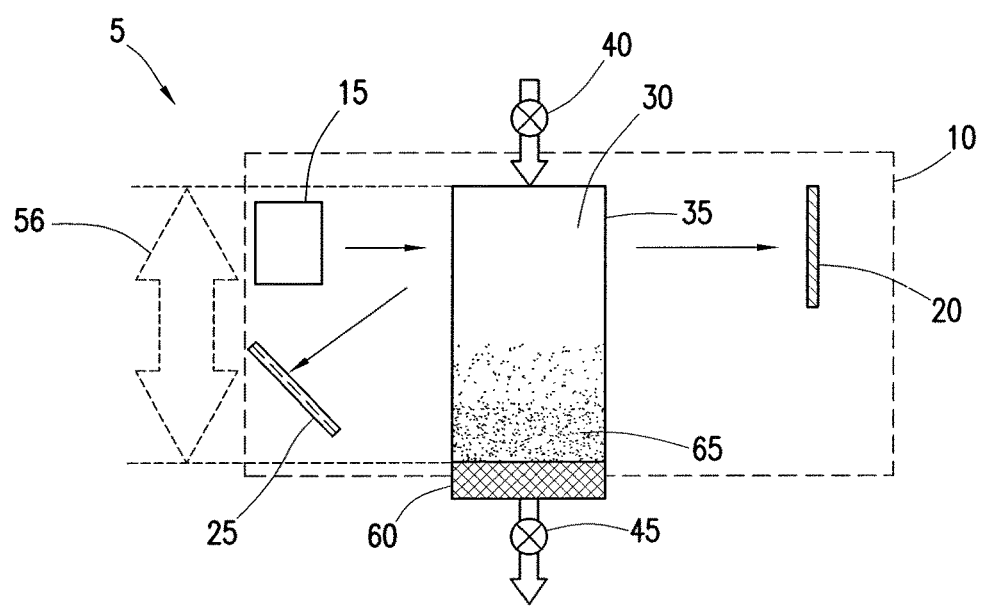
FIG. 2 is an illustration depicting an example turbidity measurement system used to test the filtering capacity of a subterranean formation.

FIG. 2 is an illustration depicting an example turbidity measurement system 5 used to test the filtering capacity of a subterranean formation. As with FIG. 1, the turbidity measurement system 5 may comprise a turbidity measurement apparatus 10 which may comprise a light source 15, at least one light detector 20, and at least one backscatter detector 25. Turbidity measurement system 5 also may comprise a vessel 35 with injection port 40 and filtrate port 45. FIG. 2 may further comprise a porous media 60. The porous media 60 may be any porous media. For example porous media may be a filter 50 (e.g., FIG. 1) designed to mimic the filtering properties of a subterranean formation of interest or the porous media 60 may be a cross section of the subterranean formation of interest (e.g., a core sample). Moreover, if it is desirable to test the flow of a fractured subterranean formation, a section of subterranean formation may be fractured and then used.

In the method described by the example of FIG. 2, the filter cake 65 formation may be one area of interest. Filter cake 65 is the residue that forms at the interface between the wellbore fluid 30 and the porous media 60. As wellbore fluid 30 passes through porous media 60, solids suspended in wellbore fluid 30 that are too large, or are otherwise incapable of passing through porous media 60, may deposit on the surface of porous media 30. The residue formed from this solid deposition is the filter cake 65. There are many variables that may affect the formation of a filter cake including the amount of contact a wellbore fluid has with a formation, the pressure of the system, the type of subterranean formation, the solids volume fraction of the wellbore fluid, the chemical and physical properties of the wellbore fluid, and the chemical and physical properties of the subterranean formation. The dynamics in which these properties affect the formation of filter cake 65 may be analyzed by turbidity measurement system 5.

Continuing with FIG. 2, wellbore fluid 30 may be injected into the interior of vessel 35 via injection port 40. Wellbore fluid 30 may be injected into vessel 35 under pressure if desired. As wellbore fluid 30 enters the interior of vessel 35, at least a portion of wellbore fluid 30 may begin to flow through porous media 60 and then out of vessel 35 via filtrate port 45. If wellbore fluid 30 comprises suspended solids, a portion of said suspended solids may deposit at the interface of wellbore fluid 30 and porous media 60 forming filter cake 65. Turbidity measurement apparatus 10 may continuously scan a portion of, or the entirety of the length and/or width of the vessel 35 as illustrated by arrow 56 providing real time updates of the dynamics of the suspended solids present in the wellbore fluid 30 over time. In a continuous process, the turbidity measurement of the wellbore fluid 30 may increase over time should the depth and density of the filter cake increase. Alternatively, should the interaction between the porous media 60 and the wellbore fluid 30 not allow for sufficient filter cake formation, the relative amount of turbidity in the wellbore fluid 30 may remain close to constant. As such, the overall values describing the permeability and porosity of the porous media 60 may be studied in real time as the porous media 60 interacts with wellbore fluid 30. Further, the variables of filter cake 65 formation that were discussed above, e.g., pressure of the system, amount of contact, etc., may be altered to further study the dynamics of the process if desired.

Figure 3:
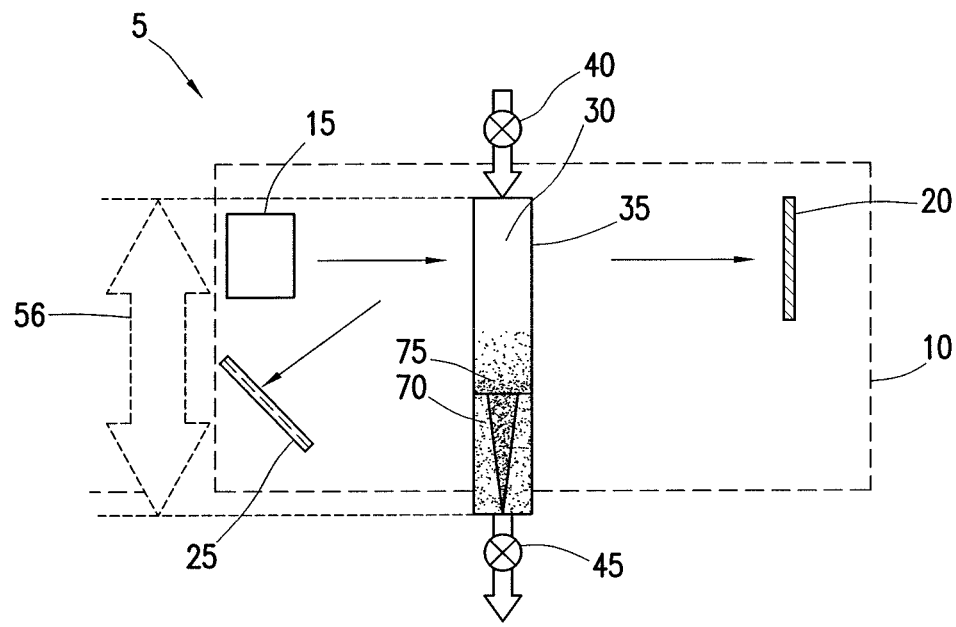
FIG. 3 is an illustration depicting an example turbidity measurement system used to test the dynamics of wellbore fluid additives with a fractured media.

FIG. 3 is an illustration depicting an example turbidity measurement system 5 used to test the dynamics of wellbore fluid additives with a fractured media. As with FIG. 1, the turbidity measurement system 5 may comprise a turbidity measurement apparatus 10 which may comprise a light source 15, at least one light detector 20, and at least one backscatter detector 25. Turbidity measurement system 5 also comprises a vessel 35 with injection port 40 and filtrate port 45. FIG. 3 further comprises a fractured media 70. Fractured media 70 may include media that has one or more slots, fractures, channels, tunnels, or other flow paths, etc. that may mimic fractures that could be encountered in a fractured subterranean formation. The fractured media 70 may be any media comprising a fracture 75. While not illustrated, the fracture media 70 may comprise more than one fracture 75, as desired for a particular application. The fractured media 70 may be made from transparent materials such as transparent glass or plastics. The fracture 75 may be formed in the fractured media 70 to mimic a fracture in a subterranean formation.

In the method described by the example of FIG. 3, the effect of wellbore additives may be one area of interest. Interaction between different types of wellbore additives and the fractured media 70 may be studied by the method illustrated in FIG. 3. In applications using lost circulation materials, wellbore fluid 30 may comprise lost circulation materials. The lost circulation materials may be any such lost circulation materials suitable for analysis with the turbidity measurement apparatus 10. Examples of lost-circulation materials that may be used include a wide variety of particulate materials, including, but are not limited to, cedar bark, shredded cane stalks, mineral fiber, mica flakes, cellophane, calcium carbonate, ground rubber, polymeric materials, pieces of plastic, grounded marble, wood, nut hulls, plastic laminates (Formica® laminate), corncobs, and cotton hulls.

With continued reference to FIG. 3, wellbore fluid 30 may be injected into the interior of vessel 35 via injection port 40. Wellbore fluid 30 may be injected into vessel 35 under pressure if desired. As wellbore fluid 30 enters the interior of vessel 35, at least a portion of wellbore fluid 30 may begin to flow through fractured media 70 and then out of vessel 35 via filtrate port 45. At least a portion The lost circulation materials suspended within wellbore fluid 30 may deposit at the face of the fractured media 70 or may deposit within the fracture 75 in the fractured media 70. The lost circulation materials deposited at the opening and throughout fractured media 70 may bridge the fracture and to some extent may seal the fracture 75 from the wellbore fluid 30. A particle pack comprising the lost circulation materials may form in the fracture 75. Turbidity measurement apparatus 10 may continuously scan a portion of, or the entirety of the length and/or width of the vessel 35 as illustrated by arrow 56 providing real time updates of the dynamics of the circulation materials present in the wellbore fluid 30 and the fractured media 70 over time. Turbidity measurement apparatus 10 may measure whether the lost circulation materials are depositing at the opening and/or within fractured media 70. The wellbore fluid 30 may be injected continuously if desired so that the dynamics of the continuous build-up of lost circulation materials may be monitored.

With continued reference to FIG. 3, in applications using hydraulic fracturing techniques, wellbore fluid 30 may comprise proppant. The proppant may be any such proppant suitable for analysis with the turbidity measurement apparatus 10. Wellbore fluid 30 comprising proppant may be injected into the interior of vessel 35 via injection port 40. Wellbore fluid 30 may be injected into vessel 35 under pressure if desired. As wellbore fluid 30 enters the interior of vessel 35, at least a portion of wellbore fluid 30 may begin to flow through fractured media 70 and then out of vessel 35 via filtrate port 45. The proppant suspended within wellbore fluid 30 may deposit at the face of fractured media 70 or may deposit within the fracture 75 in the fractured media 70. Turbidity measurement apparatus 10 may continuously scan a portion of, or the entirety of the length and/or width of the vessel 35 as illustrated by arrow providing real time updates of the dynamics of the proppant present in the wellbore fluid 30 and the fractured media 70 over time. Turbidity measurement apparatus 10 may measure whether the proppant is depositing at the opening and/or within fractured media 70. The wellbore fluid 30 may be injected continuously if desired so that the dynamics of the continuous build-up of proppant may be monitored. This method may allow for the efficient selection of different sizes and/or types of proppant based on the size of the fracture. Other types of solids may also be suspended in the wellbore fluid 30 in place of or in addition to the lost circulation materials and/or proppant as desired for a particular application.

Figure 4:
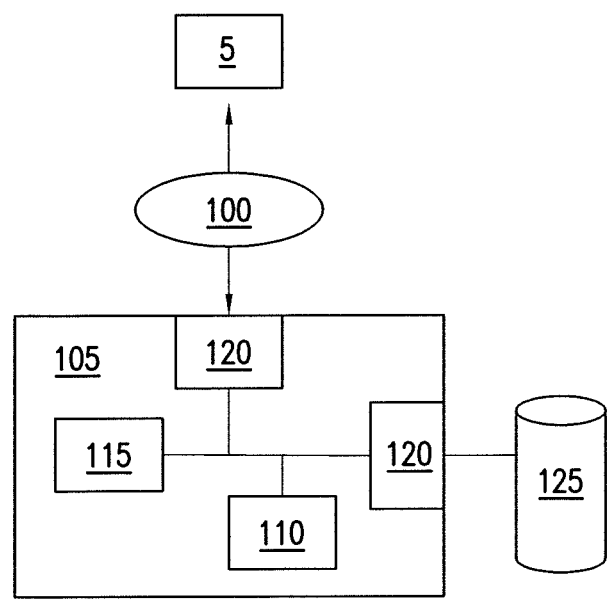
FIG. 4 is an illustration of an example turbidity measurement system communicatively coupled to a computer system.

FIG. 4 illustrates the connection of the turbidity measurement system 5 to one example of an external computer system 105 via communication link 100. Communication link 100 may include a direct connection, a private network, a virtual private network, a local area network, a WAN (e.g., an Internet-based communication system), a wireless communication system (e.g., a satellite communication system, telephones), combinations thereof, or any other suitable communication link. Computer system 105 may be any suitable data processing system, including computer systems, handheld devices, or any other suitable device. A suitable data processing system may include processor 110, memory 115, and software operable on processor 110 to process and analyze the measurement data generated by turbidity measurement system 5, adjust the parameters of turbidity measurement system 5, and/or operate turbidity measurement system 5. Computer system 105 may comprise a processor 110, memory 115, and input/output ("I/O") interface(s) 120. Processor 110 may comprise one central processing unit or may be distributed across one or more processors in one or more locations. Memory 115 should be communicatively coupled to processor 110. Memory 115 may be read-only memory, random-access memory, or the like. I/O interface(s) 120 should be communicatively coupled to processor 110. I/O interface(s) 120 may be any suitable system for connecting computer system 105 to a communication link, such as a direct connection, a private network, a virtual private network, a local area network, a wide area network ("WAN"), a wireless communication system, or combinations thereof; storage devices, such as storage 125; external devices, such as a keyboard, a monitor, a printer, a voice recognition device, or a mouse; or any other suitable system. Storage 125 may also be provided. Storage 125 may be communicatively coupled to I/O interface(s) 120 or to processor 110. Storage 125 may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for computer system 105.

Data processing and analysis software native to turbidity measurement system 5 and/or installed on computer system 105 may be used to analyze the data generated by turbidity measurement system 5. This procedure may be automated such that the analysis happens without the need for operator input or control. Further, the operator may select from several previously input parameters or may be able to recall previously measured data. Any of the data may be transferable and/or storable on a USB drive if desired.

Figure 5:
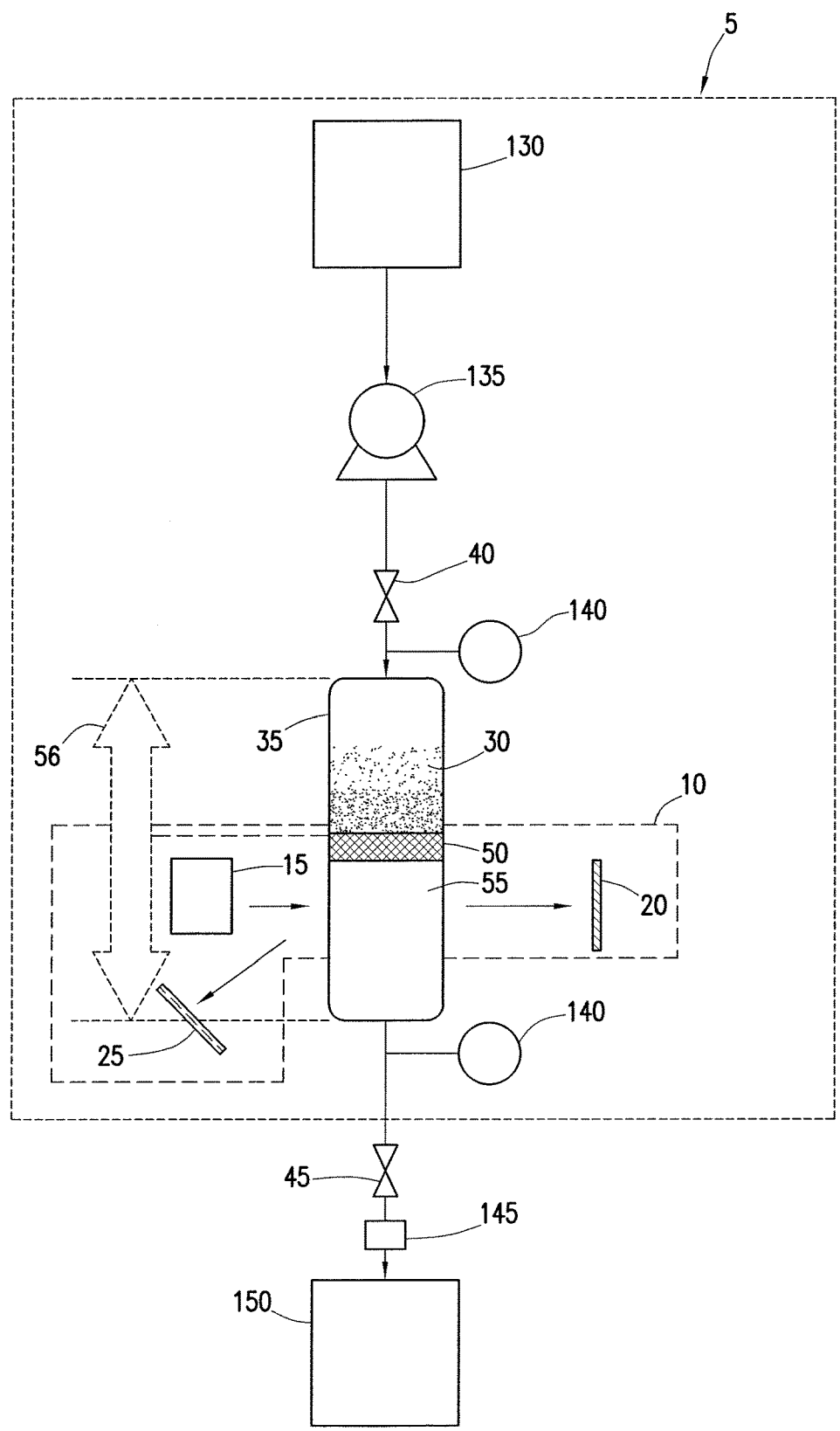
FIG. 5 is an illustration of example turbidity measurement system which comprises additional components used in the transfer and conditioning of a wellbore fluid.

FIG. 5 illustrates an example turbidity measurement system 5 which comprises additional components used in the transfer and conditioning of wellbore fluid 30. Wellbore fluid 30 may be supplied to turbidity measurement apparatus 10 via wellbore fluid supply 130. Wellbore fluid supply 130 may be any such vessel or conduit used to store and/or transport wellbore fluid 30. Without limitation, examples may include tanks, piping, and the like. Wellbore fluid supply 130 may receive wellbore fluid 30 from any upstream process. Without limitation, examples of upstream processes may include fluid recovery processes or fluid preparation processes. Wellbore fluid 30 may be pumped from wellbore fluid supply 130 by pump 135. Pump 135 may be any such pump capable of pumping wellbore fluid 30 from wellbore fluid supply 130 or another location to turbidity measurement apparatus 10. Wellbore fluid 30 may then be injected via injection port 40 into vessel 35. Optionally, a temperature measurement sensor 140 may measure the temperature of wellbore fluid 30 prior to or while wellbore fluid 30 is injected into vessel 35. Temperature measurement sensor 140 may comprise any temperature measurement sensor capable of measuring the temperature of wellbore fluid 30.

Once wellbore fluid 30 is injected into vessel 35, the turbidity measurement apparatus 10 may proceed to measure the turbidity of wellbore fluid 30 in any of the manners as described in FIGS. 1 to 3. Once the turbidity measurement apparatus 10 has completed a desired measurement, filtrate 55 may exit vessel 35 via filtrate port 45. Optionally, an additional temperature measurement sensor 140 may measure the temperature of filtrate 55 prior to or after filtrate 55 exits vessel 35 via filtrate port 45. Temperature adjustment unit 145 may adjust the temperature of filtrate 55 if desired. After exiting vessel 35, filtrate 55 may be collected in a filtrate collector 150 for use in any downstream processes. Filtrate collector 150 may be any such vessel or conduit used to store and/or transport filtrate 55. Without limitation, examples may include tanks, piping, and the like. Downstream processes may include any process downstream of turbidity measurement system 5 including drilling and well treatment processes.

A turbidity measurement system for measuring the turbidity of wellbore fluids may be provided. The turbidity measurement apparatus may include one or of the components illustrated on illustrated on FIGS. 1-5. A turbidity measurement system may comprise a vessel configured to hold a wellbore fluid, wherein a permeable obstruction to flow is positioned in the vessel; a light source positioned to direct light at the vessel; a light detector positioned to measure light intensity of light emitted by the light source and passing through the vessel; and a backscatter detector positioned to measure the light intensity of reflected light emitted from the light source. The light source, light detector, and backscatter detector may be configured to scan the entirety of the length and/or width of the vessel. The light source, light detector, and backscatter detector may not be connected together as a single unit. The vessel may comprise an injection port and a filtrate port. The permeable obstruction may comprise at least one material selection from the group consisting of a filter, porous media, or a fractured media. The porous media may be a cross section of a subterranean formation. The permeable obstruction may comprise a fracture media, wherein the fractured media is made from a transparent material. The transparent material may comprise a glass or a plastic. The turbidity measurement system may be communicatively coupled to an external computer system.

A method for measuring the turbidity of wellbore fluids may be provided. The turbidity measurement apparatus may include one or of the components illustrated on illustrated on FIGS. 1-5. A method for measuring the turbidity of a wellbore fluid may comprise injecting a volume of wellbore fluid into the interior of a vessel, wherein a permeable obstruction to flow is positioned in the vessel; and measuring the turbidity of the wellbore fluid with a turbidity measurement apparatus, wherein the turbidity measurement apparatus comprises a light source, a light detector, and a backscatter detector. The turbidity measurement apparatus may scan the entirety of the length and/or width of the vessel. The light source, light detector, and backscatter detector may not be connected together as a single unit. The permeable obstruction may be a cross section of a subterranean formation. The wellbore fluid may be a drilling fluid. The wellbore fluid may comprise a lost circulation material. The wellbore fluid may comprise a proppant. The wellbore fluid may comprise suspended solids that form a filter cake on a face of the permeable obstruction. The permeable obstruction may comprise a fractured media. The wellbore fluid may comprise suspended solids that form a pack in the fractured media. The turbidity measurement system may be communicatively coupled to an external computer system.

The preceding description provides various embodiments of turbidity measurement systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A turbidity measurement system comprising:
    a vessel configured to hold a wellbore fluid, wherein the vessel comprises a flow path for the wellbore fluid;
    a permeable obstruction to flow positioned in the fluid flow path within the vessel, wherein the permeable obstruction comprises at least one obstruction selected from the group consisting of a subterranean formation sample, a fractured subterranean formation sample, and a fractured media;
    a light source positioned to direct light at the vessel, wherein the light is directed to pass through the vessel at a position before and after the permeable obstruction;
    a light detector positioned to measure light intensity of light emitted by the light source passing through the vessel; and
    a backscatter detector positioned to measure the light intensity of reflected light emitted from the light source.

2. A system according to claim 1, wherein the light source, light detector, and backscatter detector are configured to scan an entirety of the length and/or width of the vessel.

3. A system according to claim 1, wherein the light source, light detector, and backscatter detector are not connected together as a single unit.

4. A system according to claim 1, wherein the vessel comprises an injection port and a filtrate port.

5. A system according to claim 1, wherein the permeable obstruction is a cross section of a subterranean formation.

6. A system according to claim 1, wherein the permeable obstruction comprises the fractured media, wherein the fractured media is made from a transparent material.

7. A system according to claim 6, wherein the transparent material comprises a glass or a plastic.

8. A system according to claim 1, wherein the turbidity measurement system is communicatively coupled to an external computer system.

9. A method for measuring the turbidity of a wellbore fluid comprising:
- injecting a volume of a wellbore fluid into a vessel, wherein the vessel comprises a flow path for the wellbore fluid, wherein a permeable obstruction to flow is positioned in the vessel in the fluid flow path, and wherein the permeable obstruction comprises at least one obstruction selected from the group consisting of a subterranean formation sample, a fractured subterranean formation sample, and a fractured media;
- passing light from a light source though the vessel, wherein the light is directed to pass through the vessel at a position before and after the permeable obstruction;
- detecting the light with a light detector and backscatter detector, the light detector positioned to measure light intensity of light emitted by the light source passing through the vessel and the backscatter detector positioned to measure the light intensity of reflected light emitted from the light source;
- determining a turbidity of the wellbore fluid before the permeable obstruction; and
- determining a turbidity of the wellbore fluid after the permeable obstruction.

10. A method according to claim 9, wherein the light source, light detector, and backscatter detector are not connected together as a single unit.

11. A method according to claim 9, wherein the wellbore fluid is a drilling fluid.

12. A method according to claim 9, wherein the wellbore fluid comprises lost circulation materials.

13. A method according to claim 9, wherein the wellbore fluid comprises a proppant.

14. A method according to claim 9, wherein the wellbore fluid comprises suspended solids that form a filter cake on a face of the permeable obstruction.

15. A method according to claim 9, wherein the permeable obstruction comprises the fractured media, and wherein the fractured media comprises an optically transparent material.

16. A method according to claim 15, wherein the wellbore fluid comprises suspended solids that form a pack in the fractured media.

17. A method according to claim 9, wherein the turbidity measurement system is communicatively coupled to an external computer system.

* * * * *